(12) United States Patent
Khasanov et al.

(10) Patent No.: US 8,940,434 B2
(45) Date of Patent: Jan. 27, 2015

(54) ELECTROLYTE ADDITIVE AND ELECTROLYTE AND LITHIUM RECHARGEABLE BATTERY INCLUDING SAME

(71) Applicant: Samsung SDI Co., Ltd., Yongin-si, Gyeonggi-do (KR)

(72) Inventors: Makhmut Khasanov, Yongin-si (KR); Woo-Cheol Shin, Yongin-si (KR); Denis Chernyshov, Yongin-si (KR); Alexey Tereshchenko, Yongin-si (KR); Vladimir Egorov, Yongin-si (KR); Pavel Shatunov, Yongin-si (KR)

(73) Assignee: Samsung SDI Co., Ltd., Yongin-si, Gyeonggi-do (KR)

(*) Notice: Subject to any disclaimer, the term of this patent is extended or adjusted under 35 U.S.C. 154(b) by 0 days.

(21) Appl. No.: 13/829,736

(22) Filed: Mar. 14, 2013

(65) Prior Publication Data

US 2014/0134480 A1 May 15, 2014

(30) Foreign Application Priority Data

Nov. 13, 2012 (KR) ........................ 10-2012-0128161

(51) Int. Cl.
*H01M 6/04* (2006.01)
*C07C 331/28* (2006.01)
*H01M 10/052* (2010.01)
*H01M 10/056* (2010.01)

(52) U.S. Cl.
CPC ........... *C07C 331/28* (2013.01); *H01M 10/052* (2013.01); *H01M 10/056* (2013.01); *Y02E 60/122* (2013.01)

USPC ............ 429/200; 429/188; 429/314; 429/339

(58) Field of Classification Search
USPC .................................. 429/200, 188, 314, 339
See application file for complete search history.

(56) References Cited

U.S. PATENT DOCUMENTS

| | | | |
|---|---|---|---|
| 5,650,244 | A | 7/1997 | Shoji et al. |
| 6,905,762 | B1 | 6/2005 | Jow et al. |
| 7,824,578 | B2 | 11/2010 | Lee et al. |
| 2011/0052953 | A1 | 3/2011 | Saito et al. |

FOREIGN PATENT DOCUMENTS

| | | |
|---|---|---|
| JP | 06-333596 | 12/1994 |
| JP | 07-176323 | 7/1995 |
| JP | 07-320779 | 12/1995 |
| JP | 08-064238 A | 3/1996 |
| JP | 08-321312 | 12/1996 |

(Continued)

OTHER PUBLICATIONS

Pallavi Verma, Pascal Maire and Petr Novák, A review of the features and analyses of the solid electrolyte interphase in Li-ion batteries, Review Article, 2010, pp. 6332-6341, Electrochimica Acta.

(Continued)

*Primary Examiner* — Jane Rhee
(74) *Attorney, Agent, or Firm* — Knobbe Martens Olson & Bear LLP

(57) ABSTRACT

Disclosed are an additive for a rechargeable lithium battery electrolyte including an aromatic compound having an isothiocyanate group (—NCS), and an electrolyte and rechargeable lithium battery including the same.

16 Claims, 3 Drawing Sheets

(56) References Cited

FOREIGN PATENT DOCUMENTS

| | | |
|---|---|---|
| JP | 09-073918 | 3/1997 |
| JP | 2005194511 A * | 7/2005 |
| KR | 10-2011-0021662 | 3/2001 |
| KR | 1020070031807 A | 3/2007 |

OTHER PUBLICATIONS

Sheng Shui Zhang, A review on electrolyte additives for lithium-ion batteries, Journal of Power Sources, 2006, pp. 1379-1394, ScienceDirect.

* cited by examiner

ELECTROLYTE ADDITIVE AND ELECTROLYTE AND LITHIUM RECHARGEABLE BATTERY INCLUDING SAME

CROSS-REFERENCE TO RELATED APPLICATIONS

This application claims priority to and the benefit of Korean Patent Application No. 10-2012-0128161 filed in the Korean Intellectual Property Office on Nov. 13, 2012, the entire contents of which are incorporated herein by reference.

BACKGROUND

1. Field

This disclosure relates to an additive for a rechargeable lithium battery electrolyte, an electrolyte for a rechargeable lithium battery, and a rechargeable lithium battery including the same.

2. Description of the Related Technology

Relating to the recent tendency of down sizing and weight lightening of portable electronic devices, batteries used for a power source thereof are required to have a higher performance and a larger capacity. The commercially available rechargeable lithium battery has an average discharge potential of 3.7V, or around 4V, which is the essential item of the digital generation including a cellular phone, a laptop computer, a camcorder or the like, which are called 3C.

The rechargeable lithium battery is fabricated by using a material capable of reversibly intercalating/deintercalating lithium ion as a positive active material and a negative active material; injecting a liquid electrolyte or a polymer electrolyte between the positive electrode and the negative electrode. The rechargeable lithium battery includes a positive active material of lithium-transition metal oxide and a negative active material of lithium metal, lithium alloy, carbon (crystalline or amorphous) or carbon composite.

As the battery shows the characteristics by the complex reaction of a positive electrode/electrolyte, a negative electrode/electrolyte solution, and so on, using an appropriate electrolyte is one of important factors for improving the battery performance. When using a liquid electrolyte, an organic solvent having a low boiling point is used to enhance the low temperature performance. In this case, the organic solvent having a low boiling point is decomposed under the condition of allowed to stand at a high temperature, so as to occur a swelling phenomenon that the prismatic battery or pouch are swelled. Thereby, it may cause problems of deteriorating the battery reliability and safety at a high temperature.

In order to solve the problems, a vent or a current breaker may be provided to discharge the inner electrolyte solution when increasing the inner pressure at greater than or equal to the predetermined level, thus the rechargeable battery including the non-aqueous electrolyte solution may improve the safety. However, it may cause problems of miss-operation due to the inner pressure increase.

In addition, to suppress the inner pressure increase, it is known that the additives are injected to the electrolyte solution to change the SEI (Solid Electrolyte Interface) film forming reaction. For example, Japanese Patent Laid-Open Publication No. 9-73918 discloses a method of improving battery storability at a high temperature by adding less than or equal to 1% of diphenyl picrylhydrazyl compound; Japanese Patent Laid-Open Publication No. Hei. 8-321312 discloses a method of improving the cycle-life performance and the long-term storability by using 1%-20% of N-butyl amine compound in an electrolyte solution; Japanese Patent Laid-Open Publication No. Hei. 8-64238 discloses a method of improving the battery storability by adding $3 \times 10^{-4}$ to $3 \times 10^{-3}$ moles of calcium salt; Japanese Patent Laid-Open Publication No. Hei. 6-333596 discloses a method of improving the battery storability by adding an azo compound to suppress the reaction of between the electrolyte solution and the negative electrode. In addition, Japanese Patent Laid-Open Publication No. Hei. 7-176323 discloses a method of adding $CO_2$ into the electrolyte solution; Japanese Patent Laid-Open Publication No. Hei. 7-320779 discloses a method of suppressing the decomposition of electrolyte solution by adding a sulfide-based compound into an electrolyte solution.

In order to improve the battery storability and stability, an appropriate film such as SEI film is provided on the negative electrode surface by adding a small amount of an organic material or an inorganic material. However, the added compound may be decomposed or may form an unstable film by interacting with the negative electrode of carbon at the initial charge and discharge according to the inherent electrochemical characteristics. Resultantly, the ion transportation is deteriorated in the battery, and gas is generated in the battery, and the inner pressure is increased even to deteriorate the storability, stability, cycle-life characteristics, and capacity of battery.

SUMMARY

One embodiment provides an additive for a rechargeable lithium battery electrolyte being capable of improving charge and discharge characteristics and cycle-life characteristics.

Another embodiment provides an electrolyte for a rechargeable lithium battery including the additive.

Yet another embodiment provides a rechargeable lithium battery having improved charge and discharge characteristics and cycle-life characteristics due to the electrolyte.

According to one embodiment, an additive for a rechargeable lithium battery electrolyte including an aromatic compound having an isothiocyanate group (—NCS) is provided.

The aromatic compound may be represented by the following Chemical Formula 1.

[Chemical Formula 1]

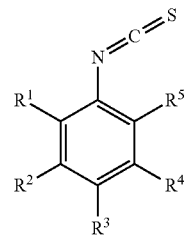

In Chemical Formula 1,
$R^1$, $R^2$, $R^3$, $R^4$, and $R^5$ are independently, hydrogen, substituted or unsubstituted C1 to C30 alkyl group, —$OR_6$, —CN, —$NO_2$, —F, —NCS, —$CF_3$, —$COR_7$, —$COOR_8$, wherein $R_6$ to $R_8$ are independently a substituted or unsubstituted $C_1$ to $C_{30}$ alkyl group.

The aromatic compound may be selected from phenyl isothiocyanate, 4-nitrophenyl isothiocyanate, trifluoromethyl phenyl isothiocyanate, 4-cyanophenyl isothiocyanate, 4-methoxyphenyl isothiocyanate, 4-fluorophenyl isothiocyanate, 4-methylphenyl isothiocyanate, 2-fluoro-5-(trifluoromethyl)phenyl isothiocyanate, 4-methyl-3-(trifluoromethyl)phenyl isothiocyanate, 4-fluoro-3-(trifluoromethyl)

phenyl isothiocyanate, 3,5-bis(trifluoromethyl)phenyl isothiocyanate, and 1,4-phenylene diisothiocyanate.

According to another embodiment, an electrolyte for a rechargeable lithium battery including a non-aqueous organic solvent, a lithium salt, and an aromatic compound having an isothiocyanate group (—NCS) is provided.

The aromatic compound may be represented by the following Chemical Formula 1.

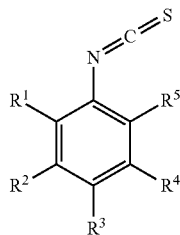

[Chemical Formula 1]

In Chemical Formula 1, $R^1$, $R^2$, $R^3$, $R^4$ and $R^5$ are independently, hydrogen, substituted or unsubstituted C1 to C30 alkyl group, —$OR_6$, —CN, —$NO_2$, —F, —NCS, —$CF_3$, —$COR_7$, —$COOR_8$, wherein $R_6$ to $R_8$ are independently a substituted or unsubstituted $C_1$ to $C_{30}$ alkyl group.

The aromatic compound may be selected from phenyl isothiocyanate, 4-nitrophenyl isothiocyanate, trifluoromethyl phenyl isothiocyanate, 4-cyanophenyl isothiocyanate, 4-methoxyphenyl isothiocyanate, 4-fluorophenyl isothiocyanate, 4-methylphenyl isothiocyanate, 2-fluoro-5-(trifluoromethyl)phenyl isothiocyanate, 4-methyl-3-(trifluoromethyl)phenyl isothiocyanate, 4-fluoro-3-(trifluoromethyl)phenyl isothiocyanate, 3,5-bis(trifluoromethyl)phenyl isothiocyanate, and 1,4-phenylene diisothiocyanate.

The aromatic compound may be included in an amount of about 0.01 wt % to about 5 wt % based on the total amount of the rechargeable lithium battery electrolyte.

The aromatic compound may be included in an amount of about 0.01 wt % to about 1 wt % based on the total amount of the rechargeable lithium battery electrolyte.

The lithium salt may include at least one selected from $LiPF_6$, $LiBF_4$, $LiSbF_6$, $LiAsF_6$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein, x and y are natural numbers), LiCl, LiI, $LiB(C_2O_4)_2$ (lithium bis(oxalato)borate; LiBOB), and a combination thereof.

According to another embodiment, a rechargeable lithium battery including a positive electrode, a negative electrode, and the electrolyte is provided.

The rechargeable lithium battery may further include a solid electrolyte interface (SEI) film that is positioned on at least one surface of the positive electrode and the negative electrode and formed by electrical reduction and polymerization reaction of the aromatic compound.

By including an electrolyte containing the novel additive, the charge and discharge characteristics and the cycle-life characteristics of the rechargeable lithium battery may be improved.

DETAILED DESCRIPTION

Figure 1:
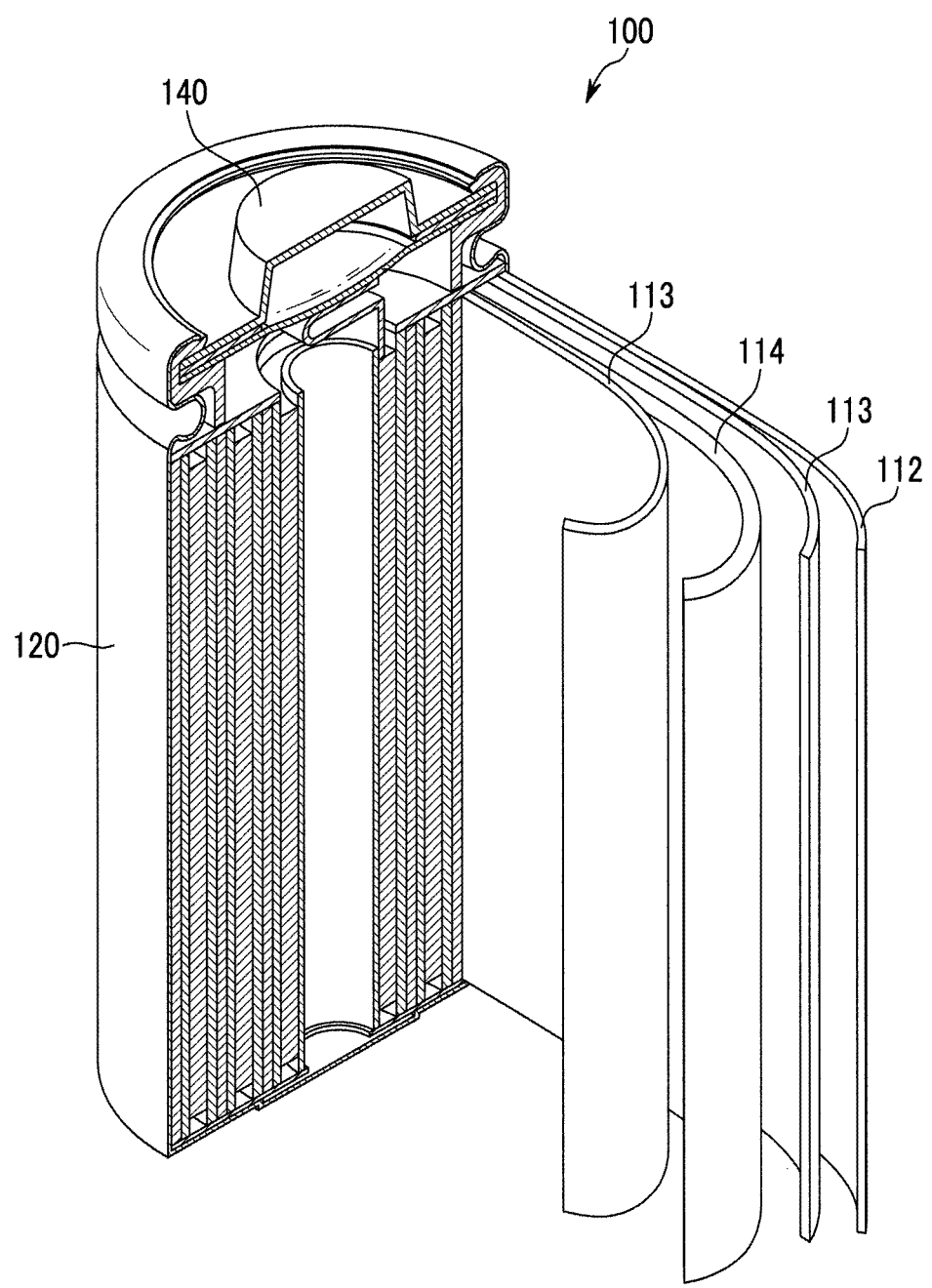
FIG. 1 is an exploded perspective view of a rechargeable lithium battery.

Example embodiments will hereinafter be described in detail. However, these embodiments are only examples, and the present embodiments are not limited thereto.

As used herein, when a definition is not otherwise provided, the term 'substituted' may refer to one substituted with a substitutent selected from a halogen (F, Br, Cl, or I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ alkoxy group, a $C_1$ to $C_{20}$ heteroalkyl group, $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when a definition is not otherwise provided, the term 'hetero' may refer to one including 1 to 3 heteroatoms selected from, N, O, S, and P.

According to one embodiment, an additive for a rechargeable lithium battery electrolyte including an aromatic compound having an isothiocyanate group (—NCS) is provided.

The aromatic compound having the isothiocyanate may effectively provide a SEI film on the negative electrode interface during the charge and discharge to suppress the cycle-life characteristic deterioration and swelling phenomenon of rechargeable lithium battery.

The aromatic compound may be represented by the following Chemical Formula 1.

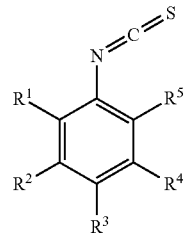

[Chemical Formula 1]

In Chemical Formula 1, $R^1$, $R^2$, $R^3$, $R^4$, and $R^5$ are independently, hydrogen, substituted or unsubstituted C1 to C30 alkyl group, —$OR_6$, —CN, —$NO_2$, —F, —NCS, —$CF_3$, —$COR_7$, —$COOR_8$, wherein $R_6$ to $R_8$ are independently a substituted or unsubstituted $C_1$ to $C_{30}$ alkyl group.

The compound represented by the above Chemical Formula 1 may be selected from phenyl isothiocyanate, 4-nitrophenyl isothiocyanate, trifluoromethyl phenyl isothiocyanate, 4-cyanophenyl isothiocyanate, 4-methoxyphenyl isothiocyanate, 4-fluorophenyl isothiocyanate, 4-methylphenyl isothiocyanate, 2-fluoro-5-(trifluoromethyl)phenyl isothiocyanate, 4-methyl-3-(trifluoromethyl)phenyl isothiocyanate, 4-fluoro-3-(trifluoromethyl)phenyl isothiocyanate, 3,5-bis(trifluoromethyl)phenyl isothiocyanate, and 1,4-phenylene diisothiocyanate, but is not limited thereto.

The aromatic compound having an isothiocyanate group is reduced and decomposed at the initial charge of rechargeable lithium battery to provide a stable SEI passivation film on a negative electrode surface, and the passivation film may improve cycle-life characteristics of rechargeable lithium battery and may suppress lowering the discharge capacity at a low temperature and swelling when allowed to stand at a high temperature.

The following Reaction Scheme 1 shows that the aromatic compound having an isothiocyanate group is polymerized to provide a SEI (solid electrolyte interface) passivation film.

[Reaction Scheme 1]

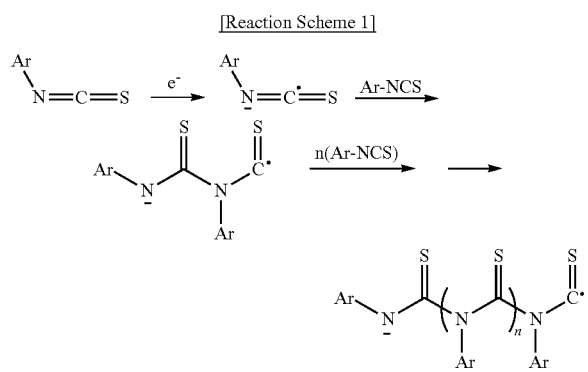

In Reaction Scheme 1, the aromatic compound having an isothiocyanate group receives electron on the negative electrode surface and is reduced to a radical, and the produced radical acts as a polymerization initiator in the polymerization reaction. In addition, since radical is continuously easily produced with the polymerization reaction, the polymerization reaction may be continuously occurred. Resultantly, a SEI film may be provided on the negative electrode surface.

On the other hand, as shown in Reaction Scheme 1, the aromatic compound having an isothiocyanate group may be used as a polymerization initiator and also used as a monomer itself participating the polymerization reaction, so as to provide a more stable and rigid SEI film within faster time compared to other additives.

In addition, the aromatic reduction voltage generally can be from about 1.4V to about 2.8 V, the reduction voltage of carbonate-based organic solvent such as ethylene carbonate (EC) is about 3.1 V which is considerably higher than the aromatic compound having an isothiocyanate group. Accordingly, on the charge and discharge, the isothiocyanate group is first reduced and decomposed before the carbonate-based organic solvent is reduced and decomposed, so as to provide a stable SEI passivation film on the negative electrode surface, thereby the carbonate-based organic solvent or the like contacting with the negative electrode surface is suppressed to be reduced and decomposed. Accordingly, even after repeating the charge and discharge, the Li ion conductivity of the initial electrolyte solution may be maintained.

For example, the compound represented by Chemical Formula 1 may be prepared in accordance with the following Reaction Scheme 2.

[Reaction Scheme 2]

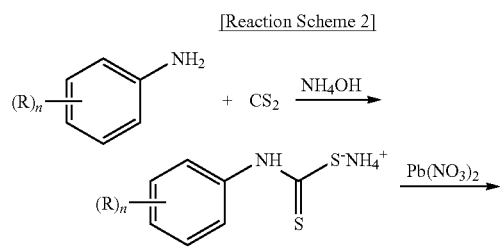

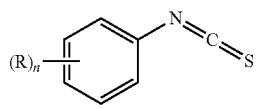

In Reaction Scheme 2, R is hydrogen, a substituted or unsubstituted C1 to C30 alkyl group, —OR$_6$, —CN, —NO$_2$, —F, —NCS, —CF$_3$, —COR$_7$, or —COOR$_8$, wherein R$_6$ to R$_8$ are independently a substituted or unsubstituted C$_1$ to C$_{30}$ alkyl group, and n is an integer from 0 to 5.

Hereinafter, a rechargeable lithium battery electrolyte including the additive for a rechargeable lithium battery electrolyte is described.

According to another embodiment provides an electrolyte for a rechargeable lithium battery including a non-aqueous organic solvent, a lithium salt and the aromatic compound having an isothiocyanate group (—NCS).

The non-aqueous organic solvent plays a role of transmitting ions taking part in the electrochemical reaction of a battery.

The non-aqueous organic solvent may include a carbonate-based, ester-based, ether-based, ketone-based, alcohol-based, or aprotic solvent. The carbonate-based solvent may include dimethyl carbonate (DMC), diethyl carbonate (DEC), dipropyl carbonate (DPC), methylpropyl carbonate (MPC), ethylpropyl carbonate (EPC), methylethyl carbonate (MEC), ethylene carbonate (EC), propylene carbonate (PC), butylene carbonate (BC), and the like, and the ester-based solvent may include methyl acetate, ethyl acetate, n-propyl acetate, dimethylacetate, methylpropionate, ethylpropionate, gamma-butyrolactone, decanolide, gamma-valerolactone, mevalonolactone, caprolactone, and the like. The ether-based solvent may include dibutyl ether, tetraglyme, diglyme, dimethoxyethane, 2-methyltetrahydrofuran, tetrahydrofuran and the like, and the ketone-based solvent may include cyclohexanone, and the like. The alcohol-based solvent may include ethanol, isopropyl alcohol, and the like. The aprotic solvent include nitriles such as R—CN (wherein R is a C$_2$ to C$_{20}$ linear, branched, or cyclic hydrocarbon group, and may include a double bond, an aromatic ring, or an ether bond), amides such as dimethylformamide, dioxolanes such as 1,3-dioxolane, sulfolanes, and the like.

The non-aqueous organic solvent may be used singularly or in a mixture. When the organic solvent is used in a mixture, its mixture ratio can be controlled in accordance with desirable performance of a battery.

The carbonate-based solvent may include a mixture of a cyclic carbonate and a linear carbonate. The cyclic carbonate and the linear carbonate are mixed together in a volume ratio of about 1:1 to about 1:9, which may enhance performance of an electrolyte.

In addition, the non-aqueous organic solvent may be prepared by further adding the aromatic hydrocarbon-based organic solvent to the carbonate-based solvent. The carbonate-based solvent and the aromatic hydrocarbon-based organic solvent are mixed together in a volume ratio of about 1:1 to about 30:1.

The aromatic hydrocarbon-based organic solvent may be an aromatic hydrocarbon-based compound represented by the following Chemical Formula 2.

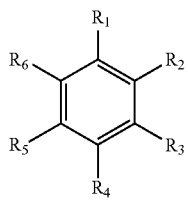

[Chemical Formula 2]

In Chemical Formula 2, $R_1$ to $R_6$ are independently hydrogen, halogen, a C1 to C10 alkyl group, a C1 to C10 haloalkyl group, or a combination thereof.

The aromatic hydrocarbon-based organic solvent may be benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 1,2-difluorotoluene, 1,3-difluorotoluene, 1,4-difluorotoluene, 1,2,3-trifluorotoluene, 1,2,4-trifluorotoluene, chlorotoluene, 1,2-dichlorotoluene, 1,3-dichlorotoluene, 1,4-dichlorotoluene, 1,2,3-trichlorotoluene, 1,2,4-trichlorotoluene, iodotoluene, 1,2-diiodotoluene, 1,3-diiodotoluene, 1,4-diiodotoluene, 1,2,3-triiodotoluene, 1,2,4-triiodotoluene, xylene, or a combination thereof.

The non-aqueous electrolyte may further include vinylene carbonate or an ethylene carbonate-based compound represented by the following Chemical Formula 3 in order to improve cycle-life of a battery.

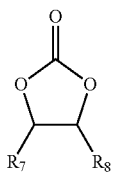

[Chemical Formula 3]

In Chemical Formula 3, $R_7$ and $R_8$ are each independently hydrogen, a halogen, a cyano group (CN), a nitro group ($NO_2$) or a C1 to C5 fluoroalkyl group, provided that at least one of $R_7$ and $R_8$ is a halogen, a cyano group (CN), a nitro group ($NO_2$) or a $C_1$ to $C_5$ fluoroalkyl group.

Examples of the ethylene carbonate-based compound include difluoro ethylenecarbonate, chloroethylene carbonate, dichloroethylene carbonate, bromoethylene carbonate, dibromoethylene carbonate, nitroethylene carbonate, cyanoethylene carbonate, fluoroethylene carbonate, and the like. The use amount of the vinylene carbonate or the ethylene carbonate-based compound for improving cycle life may be adjusted within an appropriate range.

The lithium salt is dissolved in the non-aqueous solvent and supplies lithium ions in a rechargeable lithium battery, and basically operates the rechargeable lithium battery and improves lithium ion transfer between positive and negative electrodes. The lithium salt include at least one supporting salt selected from $LiPF_6$, $LiBF_4$, $LiSbF_6$, $LiAsF_6$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein, x and y are natural numbers), LiCl, LiI, $LiB(C_2O_4)_2$ (lithium bis(oxalato)borate, LiBOB), or a combination thereof. The lithium salt may be used in a concentration of about 0.1 M to about 2.0M. When the lithium salt is included within the above concentration range, it may electrolyte performance and lithium ion mobility due to optimal electrolyte conductivity and viscosity.

The aromatic compound having an isothiocyanate group (—NCS) are the same as described above.

The aromatic compound having an isothiocyanate group may be included at about 0.01 wt % to about 5 wt %, for example, about 0.01 wt % to about 1 wt % based on the total amount of electrolyte. When included within the range, by providing the stable SEI passivation film on the negative electrode surface, the cycle-life characteristics may be improved, and the lowering discharge capacity at a low temperature and the swelling when allowed to stand at a high temperature may be suppressed.

Another embodiment provides a rechargeable lithium battery including a negative electrode; a positive electrode, and the electrolyte.

The rechargeable lithium battery may be classified as a lithium ion battery, a lithium ion polymer battery, and a lithium polymer battery according to the presence of a separator and the kind of an electrolyte used therein. The rechargeable lithium battery may have a variety of shapes and sizes and thus, may include a cylindrical, prismatic, coin, or pouch-type battery and a thin film type or a bulky type in size. The structure and fabricating method for a lithium ion battery pertaining to the present embodiments are well known in the art.

FIG. 1 is an exploded perspective view of a rechargeable lithium battery according to one embodiment. Referring to FIG. 1, the rechargeable lithium battery 100 is a cylindrical battery that includes a negative electrode 112, a positive electrode 114, a separator 113 interposed between the negative electrode 112 and the positive electrode 114, an electrolyte (not shown) impregnating the separator 113, a battery case 120, and a sealing member 140 sealing the battery case 120. The rechargeable lithium battery 100 is fabricated by sequentially laminating a negative electrode 112, a positive electrode 114, and a separator 113, spirally winding them, and housing the spirally-wound product in a battery case 120.

The positive electrode may include a current collector and a positive active material layer formed on the current collector.

The positive active material includes lithiated intercalation compounds that reversibly intercalate and deintercalate lithium ions. The positive active material may include a composite oxide including at least one selected from the group consisting of cobalt, manganese, and nickel, as well as lithium. Specific examples may be the compounds represented by the following chemical formulas:

$Li_aA_{1-b}R_bD_2$ (0.90≤a≤1.8 and 0≤b≤0.5); $Li_aE_{1-b}R_bO_{2-c}D_c$ (0.90≤a≤1.8, 0≤b≤0.5 and 0≤c≤0.05); $LiE_{2-b}R_bO_{4-c}D_c$ (0≤b≤0.5, 0≤c≤0.05); $Li_aNi_{1-b-c}Co_bR_cD_\alpha$ (0.90≤a≤1.8, 0≤b≤0.5, 0≤c≤0.05 and 0<α≤2); $Li_aNi_{1-b-c}Co_bR_cO_{2-\alpha}Z_\alpha$ (0.90≤a≤1.8, 0≤b≤0.5, 0≤c≤0.05 and 0<α≤2); $Li_aNi_{1-b-c}Co_bR_cO_{2-\alpha}Z_2$ (0.90≤a≤1.8, 0≤b≤0.5, 0≤c≤0.05 and 0<α≤2); $Li_aNi_{1-b-c}Mn_bR_cD_\alpha$ (0.90≤a≤1.8, 0≤b≤0.5, 0≤c≤0.05 and 0<α≤2); $Li_aNi_{1-b-c}Mn_bR_cO_{2-\alpha}Z_\alpha$ (0.90≤a≤1.8, 0≤b≤0.5, 0≤c≤0.05 and 0<α≤2); $Li_aNi_{1-b-c}Mn_bR_cO_{2-\alpha}Z_2$ (0.90≤a≤1.8, 0≤b≤0.5, 0≤c≤0.05 and 0<α≤2); $Li_aNi_bE_cG_dO_2$ (0.90≤a≤1.8, 0≤b≤0.9, 0≤c≤0.5 and 0.001≤d≤0.1); $Li_aNi_bCo_cMn_dGeO_2$ (0.90≤a≤1.8, 0≤b≤0.9, 0≤c≤0.5, 0≤d≤0.5 and 0.001≤e≤0.1); $Li_aNiG_bO_2$ (0.90≤a≤1.8 and 0.001≤b≤0.1); $Li_aCoG_bO_2$ (0.90≤a≤1.8 and 0.001≤b≤0.1); $Li_aMnG_bO_2$ (0.90≤a≤1.8 and 0.001≤b≤0.1); $Li_aMn_2G_bO_4$ (0.90≤a≤1.8 and 0.001≤b≤0.1); $QO_2$; $QS_2$; $LiQS_2$; $V_2O_5$; $LiV_2O_5$; $LiTO_2$; $LiNiVO_4$; $Li_{(3-f)}J_2(PO_4)_3$ (0≤f≤2); $Li_{(3-f)}Fe_2(PO_4)_3$ (0≤f≤2); and $LiFePO_4$.

In the above chemical formulae, A is Ni, Co, Mn, or a combination thereof; R is Al, Ni, Co, Mn, Cr, Fe, Mg, Sr, V, a rare earth element, or a combination thereof; D is O, F, S, P, or a combination thereof; E is Co, Mn, or a combination thereof; Z is F, S, P, or a combination thereof; G is Al, Cr, Mn, Fe, Mg, La, Ce, Sr, V, or a combination thereof; Q is Ti, Mo, Mn, or a combination thereof; T is Cr, V, Fe, Sc, Y, or a combination thereof; and J is V, Cr, Mn, Co, Ni, Cu, or a combination thereof.

The positive active material may be a compound with the coating layer on the surface or a mixture of the active material and a compound with the coating layer thereon. The coating layer may include at least one coating element compound selected from the group consisting of an oxide of the coating element, a hydroxide of the coating element, an oxyhydroxide of the coating element, an oxycarbonate of the coating element, and a hydroxycarbonate of the coating element. The compound for the coating layer may be either amorphous or crystalline. The coating element included in the coating layer may be Mg, Al, Co, K, Na, Ca, Si, Ti, V, Sn, Ge, Ga, B, As, Zr, or a mixture thereof. The coating process may include any conventional processes unless it causes any side effects on the properties of the positive active material (e.g., spray coating, immersing), which is well known to those who have ordinary skill in this art and will not be illustrated in detail.

The positive active material layer includes a binder and a conductive material.

The binder improves binding properties of the positive active material particles to one another and to a current collector. Examples of the binder include polyvinylalcohol, carboxylmethylcellulose, hydroxypropylcellulose, diacetylcellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like, but is not limited thereto.

The conductive material improves electrical conductivity of a negative electrode. Any electrically conductive material can be used as a conductive agent unless it causes a chemical change. Examples of the conductive material include natural graphite, artificial graphite, carbon black, acetylene black, ketjen black, a carbon fiber, a metal powder or a metal fiber including copper, nickel, aluminum, silver, and the like. A conductive material such as a polyphenylene derivative and the like may be mixed.

The current collector may be Al but is not limited thereto.

The negative electrode includes a current collector and a negative active material layer formed on the current collector. The negative active material layer includes a negative active material.

The negative active material includes a material that reversibly intercalates/deintercalates lithium ions, a lithium metal, a lithium metal alloy, a material being capable of doping and dedoping lithium, or a transition metal oxide.

The material that can reversibly intercalate/deintercalate lithium ions includes a carbon material. The carbon material may be any carbon-based negative active material generally used in a lithium ion rechargeable battery. Examples of the carbon material include crystalline carbon, amorphous carbon, and mixtures thereof. The crystalline carbon may be non-shaped, or sheet, flake, spherical, or fiber-shaped natural graphite or artificial graphite. The amorphous carbon may be a soft carbon, a hard carbon, a mesophase pitch carbonized product, fired coke, and the like.

Examples of the lithium metal alloy include lithium and a metal of Na, K, Rb, Cs, Fr, Be, Mg, Ca, Sr, Si, Sb, Pb, In, Zn, Ba, Ra, Ge, Al, or Sn.

The material being capable of doping and dedoping lithium may include Si, $SiO_x$ ($0<x<2$), a Si-Q alloy (wherein Q is an element selected from an alkali metal, an alkaline-earth metal, group 13 to 16 elements, a transition element, a rare earth element, or a combination thereof and is not Si), Sn, $SnO_2$, a Sn—R alloy (wherein R is an element selected from an alkali metal, an alkaline-earth metal, group 13 to 16 elements, a transition element, a rare earth element, or a combination thereof and is not Sn), and the like. At least one of these may be used as a mixture with $SiO_2$. The elements Q and R may be Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, or a combination thereof.

The transition metal oxide may include vanadium oxide, lithium vanadium oxide, and the like.

The negative active material layer also includes a binder and optionally a conductive material.

The binder improves binding properties of the positive active material particles to one another and also, with a current collector. The binder includes a non-water-soluble binder, a water-soluble binder, or a combination thereof. The non-water-soluble binder includes polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, or a combination thereof. The water-soluble binder includes a styrene-butadiene rubber, an acrylated styrene-butadiene rubber, polyvinyl alcohol, sodium polyacrylate, a copolymer of propylene and a C2 to C8 olefin, a copolymer of (meth)acrylic acid and (meth)acrylic acid alkyl ester, or a combination thereof. When the water-soluble binder is used as a negative electrode binder, a cellulose-based compound may be further used to provide viscosity. The cellulose-based compound includes one or more of carboxylmethyl cellulose, hydroxypropylmethyl cellulose, methyl cellulose, or alkali metal salts thereof. The alkali metal may be Na, K, or Li. The cellulose-based compound may be included in an amount of about 0.1 to about 3 parts by weight based on 100 parts by weight of the negative active material.

The conductive material is included to improve electrode conductivity. Any electrically conductive material may be used as a conductive material, unless it causes a chemical change. Examples of the conductive material include carbon-based materials such as natural graphite, artificial graphite, carbon black, acetylene black, ketjen black, a carbon fiber, and the like; a metal-based material such as a metal powder or a metal fiber including copper, nickel, aluminum, silver, and the like; a conductive polymer such as a polyphenylene derivative, and the like; or mixtures thereof.

The current collector may be selected from the group consisting of a copper film, a nickel film, a stainless steel film, a titanium film, a nickel foam, a copper foam, a polymer substrate coated with a conductive metal, and a combination thereof.

The negative and positive electrodes may be manufactured by a method of preparing an active material composition by mixing the active material, a conductive material, and a binder and coating the composition on a current collector. The method of manufacturing an electrode is well known and thus, is not described in detail in the present specification. The solvent includes N-methylpyrrolidone and the like but is not limited thereto. In addition, when a water-soluble binder is used for a negative electrode, water as a solvent may be used. A separator may be present between the positive electrode and negative electrode according kinds of a rechargeable lithium battery. The separator may be polyethylene, polypropylene, polyvinylidene fluoride, or a mixed multilayer of two or more layers such as a polyethylene/polypropylene double layered separator, a polyethylene/polypropylene/polyethylene triple layered separator, a polypropylene/polyethylene/polypropylene triple layered separator, and the like.

A solid electrolyte interface (SEI) layer may be provided on the surface of negative electrode and/or positive electrode by the electric reduction and polymerization reaction of the aromatic compound having an isothiocyanate group (—NCS).

The rechargeable lithium battery may be fabricated by assembling the negative electrode and/or the positive electrode obtained by the generally known method; and the electrolyte including the aromatic compound having an isothiocyanate group (—NCS), to provide an electrode assembly, and charging and discharging it for greater than or equal to one time to provide a SEI film on an active material surface. In addition, before assembling the electrode assembly, an electrode formed with SEI film already may be provided by electrically reducing the electrode fabricated according to the generally known method at a state of immersing in the electrolyte including the compounds.

The following examples illustrate the present embodiments in more detail. These examples, however, should not in any sense be interpreted as limiting the scope of the present embodiments.

Manufacture of Rechargeable Lithium Battery Cell

Example 1

A positive active material of $LiNi_{0.36}Co_{0.32}Mo_{0.32}O_2$, a polyvinylidene fluoride (PVDF), and a denka black were mixed at a weight ratio of 92.0:4.0:4.0 in an N-methylpyrrolidone solvent to provide a positive active material slurry. The positive active material slurry is uniformly coated on an aluminum current collector in a thickness of 20 μm and dried and compressed to provide a positive electrode.

97.5 wt % of graphite and 2.5 wt % of carboxymethyl cellulose/styrene-butadiene rubber (carboxymethyl cellulose:styrene-butadiene rubber=1:1.5 weight ratio) were mixed in a water solvent to provide a negative active material slurry. The negative active material slurry was coated on a copper current collector and dried, and compressed according to the general process to provide a negative electrode.

1.3 M of $LiPF_6$ was dissolved in a uniformly mixed solvent of 30 volume % of ethylene carbonate (EC), 40 volume % of ethyl methylcarbonate (EMC), 30 volume % of dimethyl carbonate (DMC) and added with 0.1 wt % of 4-nitrophenyl isothiocyanate (NPITC) represented by the following Chemical Formula 4 to provide an electrolyte.

[Chemical Formula 4]

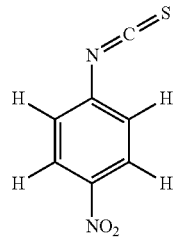

A coin-type rechargeable lithium battery cell was fabricated using the obtained positive electrode, negative electrode, and electrolyte and a porous polyethylene (PE) separator.

Example 2

A rechargeable lithium battery cell was fabricated in accordance with the same procedure as in Example 1, except that 0.05 wt % of phenyl isothiocyanate (PITC) represented by the following Chemical Formula 5 was used instead of 0.1 wt % of 4-nitrophenyl isothiocyanate (NPITC).

[Chemical Formula 5]

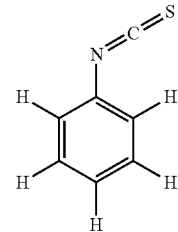

Comparative Example 1

A rechargeable lithium battery was fabricated in accordance with the same procedure as in Example 1, except that 4-nitrophenyl isothiocyanate (NPITC) was not added into the electrolyte solution.

Evaluation 1

Reduction Voltage

The rechargeable lithium battery cell obtained from Example 1 was charged at 25° C. at a 0.1 C at 4.2 V and discharged until 2.7V at a 0.1 C, and then the discharge capacity (mAh) and the potential (V) after first cycle and were measured and calculated by dQ/dV to determine the reduction potential.

Figure 2:
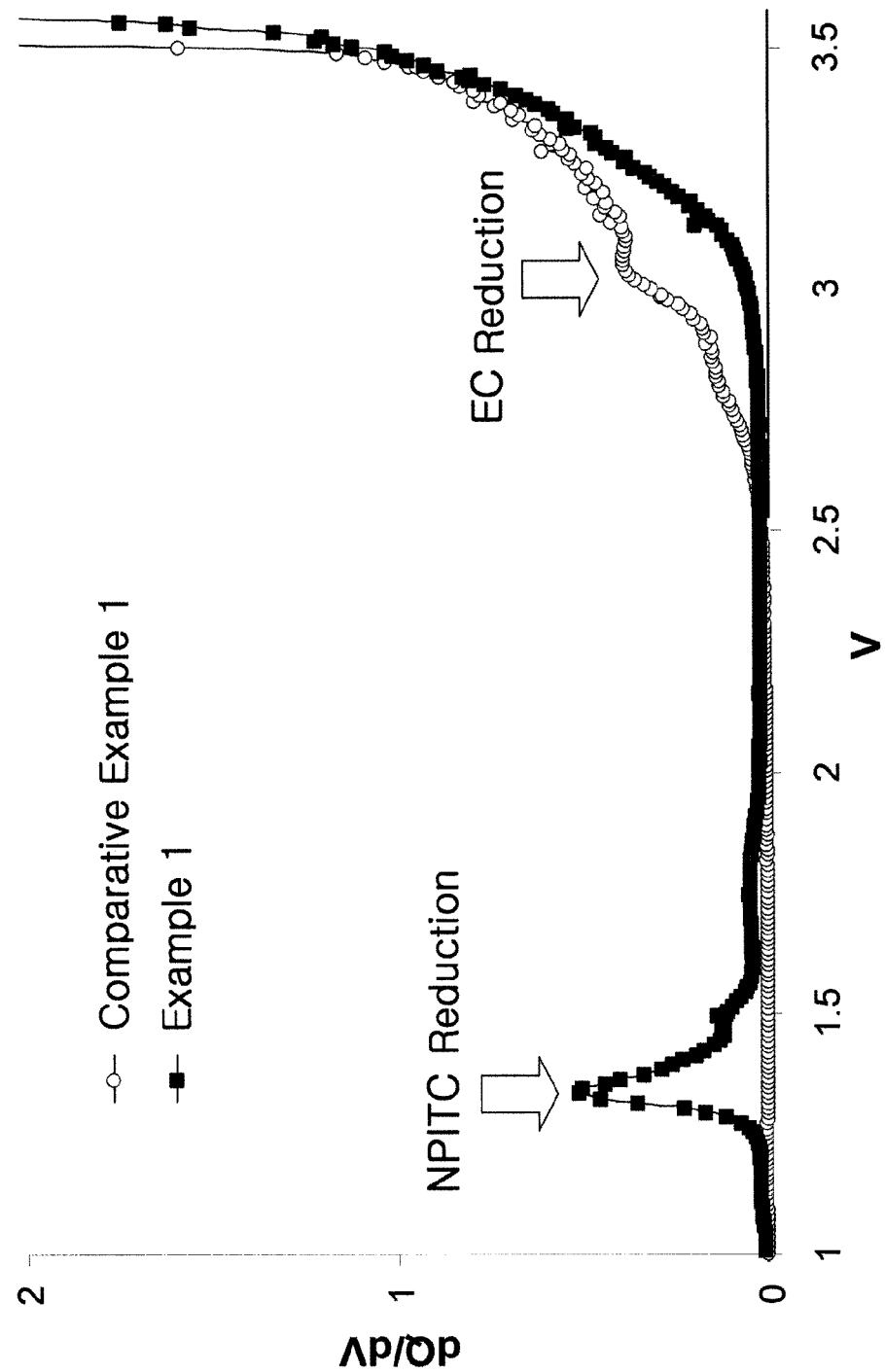
FIG. 2 is a graph showing dQ/dV results of the rechargeable lithium battery cell according to Example 1.

The dQ/dV result graph was shown in FIG. 2.

FIG. 2 is a graph showing dQ/dV results of the rechargeable lithium battery cell according to Example 1.

Referring to FIG. 2, it is confirmed that the reduction potential of 4-nitrophenyl isothiocyanate (NPITC) was about 1.3 V in the rechargeable lithium battery cell according to Example 1; and the reduction potential of ethylene carbonate (EC) according to Comparative Example 1 was about 3.1 V. Thereby, it is understood that the reduction potential of 4-nitrophenyl isothiocyanate (NPITC) was remarkably lower than the reduction potential of ethylene carbonate (EC), so it may be expected that 4-nitrophenyl isothiocyanate (NPITC) is reduced prior to the ethylene carbonate (EC) to provide a SEI film, during the first charging.

Evaluation 2

Cycle-Life Characteristic

The rechargeable lithium battery cells according to Examples 1 and 2 and Comparative Example 1 were evaluated for the cycle-life characteristics.

The rechargeable lithium battery cells according to Examples 1 and 2 and Comparative Example 1 charged and discharged for 1 cycle and 2 cycles at 25° C. and at 2.7V-4.2V and 0.1 C and 0.5 C, respectively, and then charged and discharged at 1 C to determine the capacity.

Figure 3:
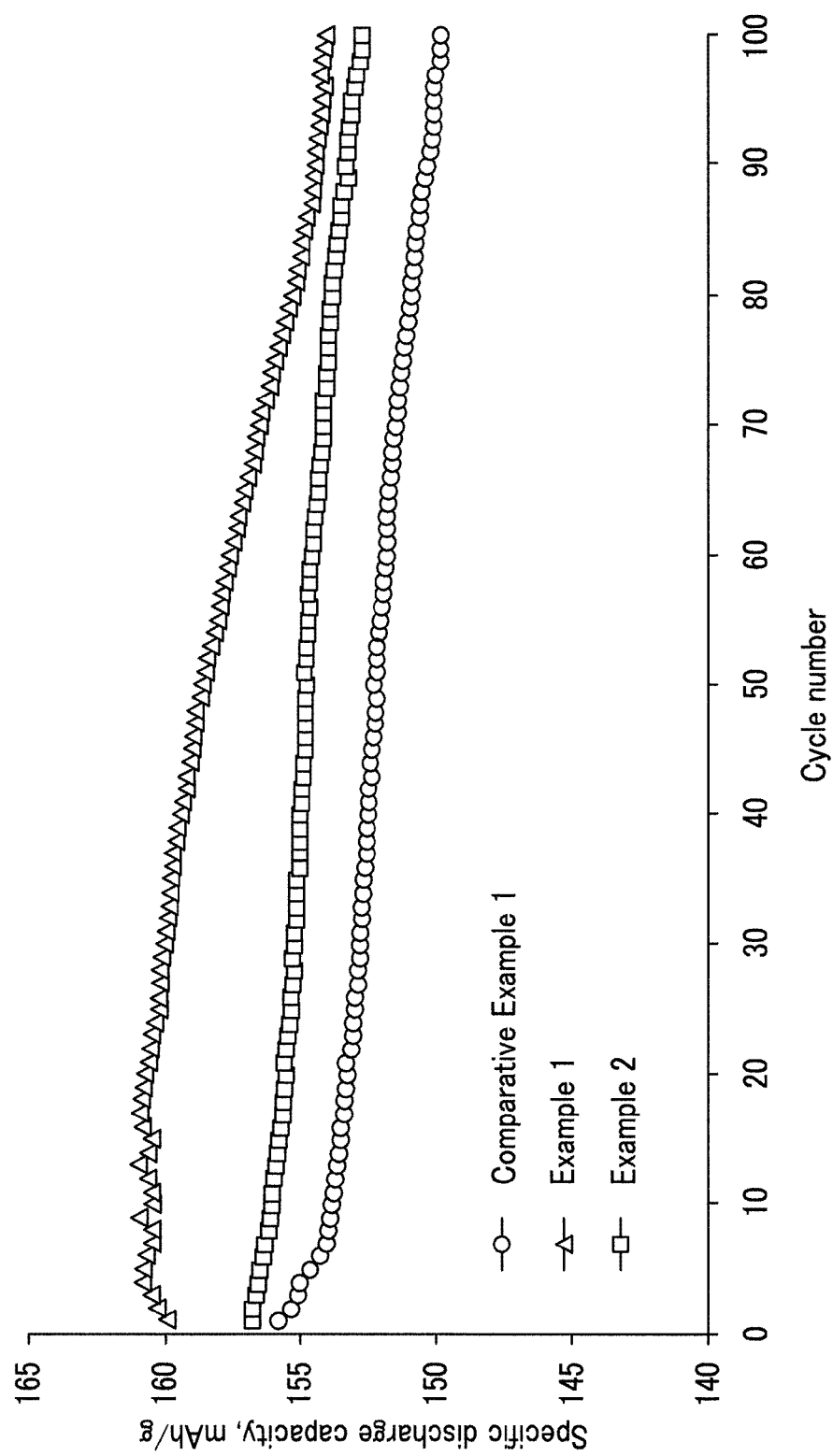
FIG. 3 is a graph showing cycle discharge capacity of rechargeable lithium battery cells according to Examples 1 and 2 and Comparative Example 1.

The results are as shown in FIG. 3.

FIG. 3 is a graph showing discharge capacity per cycles of rechargeable lithium battery cells according to Examples 1 and 2 and Comparative Example 1.

Referring to FIG. 3, the rechargeable lithium battery cells according to Examples 1 and 2 had higher remained capacity at the initial discharge capacity and after 100 cycles compared to the rechargeable lithium battery cell according to Comparative Example 1.

Thereby, it is confirmed that a stable SEI passivation film is provided on a surface of negative electrode since the electrolyte solution for a rechargeable lithium battery included an aromatic compound having an isothiocyanate group, so the cycle-life characteristics were improved.

While these embodiments have been described in connection with what is presently considered to be practical example embodiments, it is to be understood that the embodiments are not limited to the disclosed embodiments, but, on the contrary, is intended to cover various modifications and equivalent arrangements included within the spirit and scope of the appended claims.

What is claimed is:

1. An additive for a rechargeable lithium battery electrolyte, comprising an aromatic compound having an isothiocyanate group (—NCS);
    wherein the aromatic compound is selected from phenyl isothiocyanate, 4-nitrophenyl isothiocyanate, trifluoromethyl phenyl isothiocyanate, 4-cyanophenyl isothiocyanate, 4-methoxyphenyl isothiocyanate, 4-fluorophenyl isothiocyanate, 4-methylphenyl isothiocyanate, 2-fluoro-5-(trifluoromethyl)phenyl isothiocyanate, 4-methyl-3-(trifluoromethyl)phenyl isothiocyanate, 4-fluoro-3-(trifluoromethyl)phenyl isothiocyanate, 3,5-bis(trifluoromethyl)phenyl isothiocyanate, and 1,4-phenylene diisothiocyanate.

2. The additive for a rechargeable lithium battery electrolyte of claim 1, wherein the aromatic compound is represented by the following Chemical Formula 1:

[Chemical Formula 1]

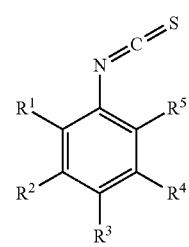

wherein,
$R^1$, $R^2$, $R^3$, $R^4$, and $R^5$ are independently, hydrogen, substituted or unsubstituted $C_1$ to $C_{30}$ alkyl group, $-OR_6$, $-CN$, $-NO_2$, $-F$, $-NCS$, $-CF_3$, $-COR_7$, $-COOR_8$, wherein $R_6$ to $R_8$ are independently a substituted or unsubstituted $C_1$ to $C_{30}$ alkyl group.

3. The additive for a rechargeable lithium battery electrolyte of claim 1, wherein the aromatic compound is represented by at least one of the following chemical formulas:

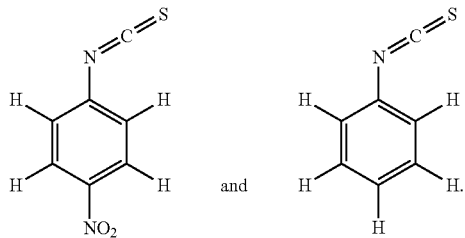

4. An electrolyte for a rechargeable lithium battery, comprising:
    a non-aqueous organic solvent,
    a lithium salt, and
    an aromatic compound having an isothiocyanate group (—NCS);
    wherein the aromatic compound is selected from phenyl isothiocyanate, 4-nitrophenyl isothiocyanate, trifluoromethyl phenyl isothiocyanate, 4-cyanophenyl isothiocyanate, 4-methoxyphenyl isothiocyanate, 4-fluorophenyl isothiocyanate, 4-methylphenyl isothiocyanate, 2-fluoro-5-(trifluoromethyl)phenyl isothiocyanate, 4-methyl-3-(trifluoromethyl)phenyl isothiocyanate, 4-fluoro-3-(trifluoromethyl)phenyl isothiocyanate, 3,5-bis(trifluoromethyl)phenyl isothiocyanate, and 1,4-phenylene diisothiocyanate.

5. The electrolyte for a rechargeable lithium battery of claim 4, wherein the aromatic compound is represented by the following Chemical Formula 1:

[Chemical Formula 1]

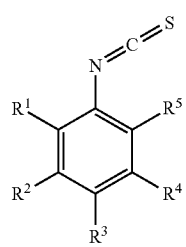

wherein,
$R^1$, $R^2$, $R^3$, $R^4$, and $R^5$ are independently, hydrogen, substituted or unsubstituted C1 to C30 alkyl group, $-OR_6$, $-CN$, $-NO_2$, $-F$, $-NCS$, $-CF_3$, $-COR_7$, $-COOR_8$, wherein $R_6$ to $R_8$ are independently a substituted or unsubstituted C1 to C30 alkyl group.

6. The electrolyte for a rechargeable lithium battery of claim 4, wherein the aromatic compound is included in an amount of about 0.01 wt % to about 5 wt % based on the total amount of the rechargeable lithium battery electrolyte.

7. The electrolyte for a rechargeable lithium battery of claim 4, wherein the aromatic compound is included in an amount of about 0.01 wt % to about 1 wt % based on the total amount of the rechargeable lithium battery electrolyte.

8. The electrolyte for a rechargeable lithium battery of claim 4, wherein the lithium salt comprises at least one selected from $LiPF_6$, $LiBF_4$, $LiSbF_6$, $LiAsF_6$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein, x and y are natural numbers), LiCl, LiI, $LiB(C_2O_4)_2$ (lithium bis(oxalato) borate; LiBOB), and a combination thereof.

9. The electrolyte for a rechargeable lithium battery of claim 4, wherein the aromatic compound is represented by at least one of the following chemical formulas:

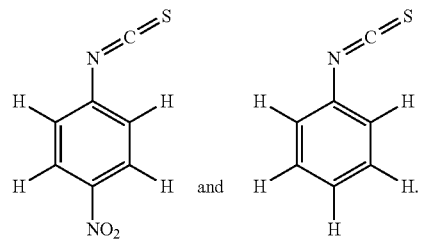

10. A rechargeable lithium battery, comprising:
    a positive electrode,
    a negative electrode, and
    an electrolyte comprising:
        a non-aqueous organic solvent,
        a lithium salt, and
        an aromatic compound having an isothiocyanate group (—NCS);

wherein the aromatic compound is selected from phenyl isothiocyanate, 4-nitrophenyl isothiocyanate, trifluoromethyl phenyl isothiocyanate, 4-cyanophenyl isothiocyanate, 4-methoxyphenyl isothiocyanate, 4-fluorophenyl isothiocyanate, 4-methylphenyl isothiocyanate, 2-fluoro-5-(trifluoromethyl)phenyl isothiocyanate, 4-methyl-3-(trifluoromethyl)phenyl isothiocyanate, 4-fluoro-3-(trifluoromethyl)phenyl isothiocyanate, 3,5-bis(trifluoromethyl)phenyl isothiocyanate, and 1,4-phenylene diisothiocyanate.

11. The rechargeable lithium battery of claim 10, wherein the rechargeable lithium battery further comprises a solid electrolyte interface (SEI) film that is positioned on at least one surface of the positive electrode and the negative electrode and formed by electrical reduction and polymerization reaction of the aromatic compound.

12. The rechargeable lithium battery of claim 10, wherein the aromatic compound is represented by the following Chemical Formula 1:

[Chemical Formula 1]

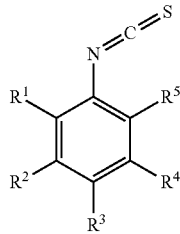

wherein,
$R^1$, $R^2$, $R^3$, $R^4$, and $R^5$ are independently, hydrogen, substituted or unsubstituted $C_1$ to $C_{30}$ alkyl group, —$OR_6$, —CN, —$NO_2$, —F, —NCS, —$CF_3$, —$COR_7$, —$COOR_8$, wherein $R_6$ to $R_8$ are independently a substituted or unsubstituted C1 to C30 alkyl group.

13. The rechargeable lithium battery of claim 10, wherein the aromatic compound is included in an amount of about 0.01 wt % to about 5 wt % based on the total amount of the rechargeable lithium battery electrolyte.

14. The rechargeable lithium battery of claim 10, wherein the aromatic compound is included in an amount of about 0.01 wt % to about 1 wt % based on the total amount of the rechargeable lithium battery electrolyte.

15. The rechargeable lithium battery of claim 10, wherein the lithium salt comprises at least one selected from $LiPF_6$, $LiBF_4$, $LiSbF_6$, $LiAsF_6$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein, x and y are natural numbers), LiCl, LiI, $LiB(C_2O_4)_2$ (lithium bis(oxalato) borate; LiBOB), and a combination thereof.

16. The rechargeable lithium battery of claim 10, wherein the aromatic compound is represented by at least one of the following chemical formulas:

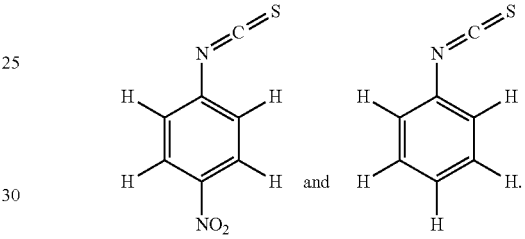

* * * * *